United States Patent [19]

Cantor et al.

[11] 4,151,275

[45] Apr. 24, 1979

[54] STABILIZED IODINE TINCTURE

[75] Inventors: Abraham Cantor, Elkins Park, Pa.; Murray W. Winicov, Flushing, N.Y.

[73] Assignee: West Laboratories, Inc., Long Island City, N.Y.

[21] Appl. No.: 841,012

[22] Filed: Oct. 11, 1977

Related U.S. Application Data

[63] Continuation of Ser. No. 693,724, Jun. 7, 1976, abandoned.

[51] Int. Cl.² ...................... A61K 31/79; A61K 33/18
[52] U.S. Cl. ........................................ 424/80; 424/150
[58] Field of Search ................................... 424/150, 80

[56] References Cited

U.S. PATENT DOCUMENTS

| | | | |
|---|---|---|---|
| 1,942,061 | 1/1934 | Hofmann | 424/150 X |
| 2,739,922 | 3/1956 | Shelanski | 424/150 X |
| 3,028,300 | 4/1962 | Cantor et al. | 424/150 X |
| 3,898,326 | 8/1975 | Cantor et al. | 424/150 X |

OTHER PUBLICATIONS

United States Pharmacopeia XIX, p. 259.
Stedman's Medical Dictionary 21st ed., 1968, p. 1647.

*Primary Examiner*—Leonard Schenkman
*Attorney, Agent, or Firm*—Howard E. Thompson, Jr.

[57] ABSTRACT

An improved iodine tincture is provided by incorporating therein a small amount, preferably about 0.25 to 2.5 parts, per part by weight of iodine, of povidone, 1-vinyl-2-pyrrolidone polymer. In these proportions, the povidone modified tincture of iodine exhibits markedly reduced tendency to burn or sensitize skin areas on which it dries, is stable, and at the same time retains the essential germicidal activity of unmodified tincture of iodine. The new products can be formulated directly, or as concentrates yielding the improved tincture upon extension with a prescribed amount of aqueous-ethanolic diluent.

2 Claims, No Drawings

STABILIZED IODINE TINCTURE

This is a continuation of application Ser. No. 693,724, filed June 7, 1976 now abandoned.

Hydroalcoholic tincture of iodine, long considered one of the most effective topical bactericidal combinations, has lost favor in recent years due to the tendency to cause chemical burns, and to its relative instability and short period of activity (P. Dineen, M.D., Drugs of Choice 1976–1977, page 139, W. Modell, ed.). This invention relates to an improvement in such tinctures of iodine whereby that instability, skin burning, and very short duration of activity, associated with the concentration and chemical reaction of the free iodine with the skin, as the hydroalcoholic solvent evaporates, is eliminated by incorporating therein a critically small amount, preferably from 0.25 to 2.5 parts, per part by weight of the iodine, of povidone, an iodine complexing polymer.

Although such povidone-iodine ratios in non-alcoholic aqueous solution are unstable and characterized by precipitation or separation, such ratios surprisingly result in stable products in appropriate hydroalcoholic iodine solutions. As the hydroalcoholic solvent in such products differentially evaporates when topically applied to the skin, and the iodine is thereby concentrated on the skin surface, the concurrently concentrating polymer further complexes the free iodine, thereby preventing the aforesaid disadvantages of, for example, Iodine Tincture USP XIX (1975). By such progressive complexing of the free iodine, as the polymer is concentrated, there is further elimination of the need for excessively high uneconomical, and functionally disadvantageous ratios such as the prior art prevailing ratio of 10 parts polymer to one part iodine (E. J. L. Lowbury and H. A. Lilly, LANCET 2:153–156, 1975; Netherlands Patent Application No. 6,410,461, Sept. 29, 1964).

Tinctures of iodine containing from about 0.25 to 20% iodine and 0.25 to 2.5 parts of water soluble inorganic iodide per part of iodine, together with 0.25 to 2.5 parts of povidone per part of iodine, in hydroalcoholic solutions containing 25–95% ethanol by volume, have been prepared and are stable. These low ratios of povidone to iodine, surprisingly, are sufficient to significantly lower the skin irritation properties of e.g. Iodine Tincture USP XIX, even though much higher ratios had been thought to be necessary and had been employed in the past.

Povidone modified iodine tinctures in accordance with the present invention can be supplied as end use products or as concentrates intended for dilution with water or aqueous ethanol by the pharmacist or consumer in preparing the end use product. A preferred end use product is Iodine Tincture USP XIX, i.e. an aqueous ethanol solution containing per 100 ml 1.8 to 2.2 gm of iodine and 2.1 to 2.6 gm of sodium iodide and containing 44 to 50% ethanol and differing therefrom only by the addition of the indicated small amounts of povidone as a pharmaceutical excipient (Example I).

Concentrates containing iodine, sodium iodide, and povidone in the above ratios, together with at least 25% ethanol by volume, can be made, which concentrates can be diluted readily with hydroalcoholic solvents (Example II). Preferred concentrates will be those containing 0.95 to 1.45 parts of sodium iodide to each part by weight of iodine so that Iodine Tincture USP XIX can be obtained by simple dilution of the concentrate with an appropriate amount of water or aqueous ethanol. To further simplify the preparation of end use products from concentrates, it is desirable that the amount of water and ethanol in the concentrate be so adjusted that the end use product is obtained by dilution with a prescribed amount of USP XIX Diluted Alcohol, the mixture of equal volumes of 95% alcohol and water which is widely used by pharmacists.

While water soluble inorganic iodide such as sodium iodide will be present in Iodine Tincture USP XIX plus povidone, it is to be understood that the addition of iodide to the formula is not essential to the present invention, and that for some purposes the iodide content of the povidone modified tincture may be derived from the elemental iodine itself. The following examples will facilitate a fuller understanding of the present invention, but it is to be understood that these examples are given by way of illustration and not of limitation.

EXAMPLE I

Five povidone modified iodine tinctures were prepared by dissolving 2.4 grams of sodium iodide, then 2.0 grams of iodine in a small amount of water, followed by 50 ml. of 95% ethanol. In five separate 25 ml. portions of water were dissolved 1.0 grams, 2.0 grams, 3.0 grams, 4.0 grams and 5.0 grams of pharmaceutical grade povidone. The resulting povidone solutions were mixed with the iodine-iodide solutions and the volumes adjusted to 100 ml. with water.

These solutions were tested for iodine complexing or distribution coefficient, D.C., by a method similar to that disclosed in U.S. Pat. No. 3,028,300, differing only in that the iodine from the hydroalcoholic phase was allowed to diffuse through a thin polyethylene film over a period of several days into the heptane phase, with results indicated in the tabulation below. If a polyethylene film is not used, some alcohol enters the heptane phase, changing the distribution constant.

Also included in the tabulation are data for a control tincture containing no povidone, and for a comparative tincture "x" in which povidone to iodine ratio is similar to the commercially available 10:1 povidone:iodine complex.

| Sample | Components (Grams) | | Povidone | Povidone/$I_2$ | D.C. |
|---|---|---|---|---|---|
| | $I_2$ | NaI | | | |
| Ia | 2 | 2.4 | 1 | .5 | 250 |
| Ib | " | " | 2 | 1.0 | 385 |
| Ic | " | " | 3 | 1.5 | 625 |
| Id | " | " | 4 | 2.0 | 750 |
| Ie | " | " | 5 | 2.5 | 1,060 |
| Control | " | " | 0 | — | 175 |
| "x" | " | " | 20 | 10.0 | >20,000 |

Attempts to prepare solutions similar to Ia through Ie using the water only as a solvent, without the aqueous ethanol, produced in each instance unsatisfactory mixtures. The very high D.C. value for sample "x" is indicative of a much lower level of free iodine than is desired in a quick acting iodine tincture.

The foregoing type products Ia through Ie are further characterized in that when applied to the skin as a topical antimicrobial, they are better area delineating agents than, for example, U.S.P. Iodine Tincture or alcoholic dilutions thereof, by virtue of the iodine color intensification associated with the povidone polymer additive. Furthermore the excessive amount of solids deposited by an application of composition "x", with its 10:1 povidone:iodine ratio is objectionable for most iodine tincture uses.

EXAMPLE II

A typical iodine tincture "concentrate" is prepared dissolving 16 gm of iodine and 19.2 gm of sodium iodide in a small amount of water adding 50 ml of 95% alcohol, dissolving therein 24.0 gm of povidone by slowly adding with stirring, and adjusting the volume of the resulting solution to 100 ml with water.

U.S.P. Iodine Tincture is then prepared by diluting 1 volume of this concentrate with 7 volumes of 50% aqueous ethanol, or, for more rapidly drying iodine tinctures, making the 1+7 (or higher) dilutions of the concentrate with 95% alcohol.

It should be noted that the concentrate can be prepared in solvent mixtures ranging from 25% to 95% aqueous ethanol in which event the diluting solvent must be appropriately selected to provide the desired ethanol concentration in the final tincture. The ethanol content of the hydroalcoholic mixture used as the solvent in the concentrate can be so chosen that dilution of the concentrate with U.S.P. "Diluted Alcohol" (a mixture of equal volumes of 95% alcohol and water) will result in U.S.P. Iodine Tincture, or so that dilution of the concentrate with 95% v/v alcohol will result in British Pharmacopeia Iodine Tincture, containing 2.5% Iodine w/v and 85% v/v ethanol.

Alternatively, the concentrates may be diluted with alcohol-water mixtures containing 25 to 95% ethanol by volume, to provide final iodine concentrations as low as 0.25% w/v.

The following tabulation provides the amounts of iodine, iodide and povidone for preparing a number of useful concentrates and indicates the dilution factor appropriate for preparation of povidone modified U.S.P. Iodine Tincture.

| Component | Concentrate | | | | | | |
|---|---|---|---|---|---|---|---|
| | a | b | c | d | e | f | g |
| Iodine % | 4.0 | 6.0 | 8 | 10.0 | 12.0 | 16.0 | 20.0 |
| NaI % | 4.8 | 7.2 | 9.6 | 12.0 | 14.4 | 19.2 | 24.0 |
| Povidone % | 6.0 | 9.0 | 12.0 | 15.0 | 18.0 | 24.0 | 30.0 |
| Solvent* | q.s to 100 ml | | | | | | |
| conc. + Diluent** | 1+1 | 1+2 | 1+3 | 1+4 | 1+5 | 1+7 | 1+9 |

*Solvent is ethanol/water solutions ranging from 25-95% ethanol.
**Diluent is ethanol/water solutions ranging from 95-25% ethanol.

In the foregoing tabulation concentrates "c" through "g" for which the dilution factors are 1+3 and higher are considered preferred concentrates for supply to pharmacists for use in their preparation of povidone modified U.S.P. iodine tincture. Concentrates "a" and "b" on the other hand can more readily be used, in special situations, as double or triple strength iodine tincture. When applied as thin layer, these concentrates can dry to provide the same deposit as heavier layers of U.S.P. tincture.

The above described concentrates have a povidone to iodine ratio of 1.5:1. It is to be understood, however, that similar concentrates can be prepared in which the povidone to iodine ratio is as low as 0.25:1 or as high as 2.5:1, (provided the total solids content does not exceed about 80%) with both the concentrates and the povidone modified iodine tinctures prepared therefrom being stable solutions.

Various changes and modifications in the povidone modified iodine tincture, and concentrates for preparing the same as herein disclosed may occur to those skilled in the art, and to the extent that such changes and modifications are embraced by the appended claims, it is to be understood that they constitute part of the present invention.

We claim:

1. A povidone modified iodine tincture comprising an aqueous ethanolic solution containing per 100 ml 1.8-2.2 grams of iodine, 2.1 to 2.6 grams of sodium iodide, an amount of povidone within the range of 0.25 to 2.5 parts per part by weight of iodine, and the amount of ethanol in said aqueous ethanolic solution being 25-95% V/V of the solvents of said modified tincture.

2. A povidone modified iodine tincture as defined in claim 1 wherein the amount of ethanol in said solution is 44-50% of said modified tincture.

* * * * *